United States Patent [19]
Liu et al.

[11] Patent Number: 6,159,985
[45] Date of Patent: Dec. 12, 2000

[54] IMIDAZO-ISOQUINOLINE COMPOUNDS, THEIR COMPOSITIONS AND USES

[75] Inventors: Song Liu, Cincinnati; David Edward Portlock, Maineville; Schwe Fang Pong, West Chester, all of Ohio

[73] Assignee: The Procter & Gamble Company, Cincinnati, Ohio

[21] Appl. No.: 09/399,475

[22] Filed: Sep. 21, 1999

[51] Int. Cl.⁷ .......................... A01N 43/42; C07D 471/00
[52] U.S. Cl. .......................... 514/292; 514/825; 514/803; 546/84; 546/86; 546/87; 546/144; 546/177
[58] Field of Search .............................. 546/84, 147, 177, 546/86, 87; 514/292, 825, 863

[56] References Cited

U.S. PATENT DOCUMENTS 3,917,610  11/1975  Takacs et al. .......................... 260/288
4,143,143   3/1979  Seiler ...................................... 424/258

OTHER PUBLICATIONS

Borchard et al., "The Positive Inotropic, Antiarrhythmic and Na+, K+–ATPase Inhibitory Effects of the Isoquinoline Derivative, BIIA", *Naunyn–Schmiedeberg's Arch. Pharmacol.*, 312 (1980) pp. 187–192.

Fox et al., "Mechanism of Inhibition of Sodium—and Potassium–Dependent Adenosine Triphosphatase by the Isoquinoline Derivative BIIA: A Specific Interaction With Sodium Activation", *Biochemical Pharmacology*, 30 (1981) pp. 611–617.

Zolyomi et al., "Potential Drugs Labelled with ¹⁴C. I. The Synthesis of 3–Benzylamino–5,6–dihydro–8,9–dimethoxy–imidazo[5,1–a]lsoquinoline hydrochloride", *J. of Labelled Compounds and Radiopharmaceuticals*, XVIII (1980) pp. 813–822.

Borchard et al., "Characterization of Antiarrhythmic Drugs by Alternating Current Induced Arrhythmias in Isolated Heart Tissues", *Arch. Int. Pharmacodyn.*, 256 (1982) pp. 253–268.

Fulop et al., "A 3–Benzilamino–5,6–dihidro–8,9–dimetoxi–imidazo–(5,1–a)–izokinolin–hidroklorid es Intermedierjei Negyszoghullamu Polarografias Vizsgalata", *Magyar Kemiai Folyoirat*, 89 (1983) pp. 293–297.

*Primary Examiner*—John Kight
*Assistant Examiner*—Raymond Covington
*Attorney, Agent, or Firm*—Milton B. Graff; Betty J. Zea; Karen F. Clark

[57] ABSTRACT

The subject invention involves compounds having the structure:

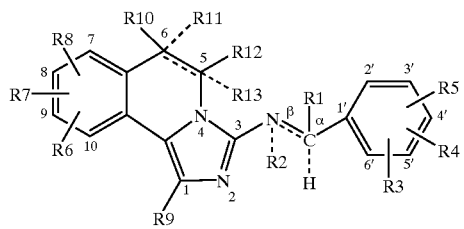

wherein the $C_\alpha$–$N_\beta$ and $C_5$–$C_6$ bonds are independently single or double bonds, R1 is selected from alkyl, aryl, and heterocycle; R2–R13 are independently selected from hydrogen and other substituents; and pharmaceutically-acceptable salts thereof. The subject invention also involves pharmaceutical compositions containing such compounds, and methods for treating or preventing diseases and disorders using such compounds.

25 Claims, No Drawings

IMIDAZO-ISOQUINOLINE COMPOUNDS, THEIR COMPOSITIONS AND USES

FIELD OF THE INVENTION

The subject invention relates to novel N-phenyl-(substituted)-methyl-5,6-dihydro-imidazo[5,1-a] isoquinolin-3-amine compounds, phannaceutical compositions containing them, and their therapeutic or preventative use in the areas of cardiovascular, oncology, infectious and inflammatory diseases.

BACKGROUND

Certain imidazo-isoquinoline compounds are disclosed in U.S. Pat. No. 3,917,610 issued Nov. 4, 1975; they are reported to have certain cardiovascular activities. One such compound is further reported on in Borchard, Fox, and Greeff, "The Positive Inotropic, Antiarrhythmic and $Na^+$, $K^+$-ATPase Inhibitory Effects of the Isoquinoline Derivative, BIIA", *Achives of Pharmacology*, vol. 312 (1980), pp. 187–192.

SUMMARY OF THE INVENTION

The subject invention includes compounds having the structure:

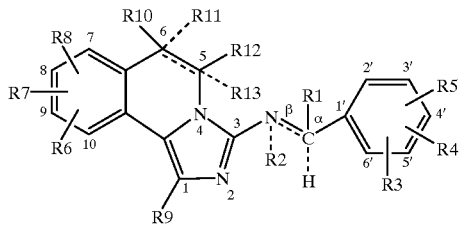

wherein:
 (a) The bond between $C_\alpha$ and $N_\beta$ is a single bond, or a double bond whereby R2 (and H on $C_\alpha$) are nil;
 (b) the bond between $C_5$ and $C_6$ is a single bond, or a double bond wherein R11 and R13 are nil;
 (c) R1 is selected from alkyl, aryl, and heterocycle;
 (d) R2, if not nil, is selected from hydrogen, alkyl, alkylacyl, arylacyl, alkylsulfonyl and arylsulfonyl;
 (e) R3, R4 and R5 are each independently selected from hydrogen, halo, alkyl, aryl, heterocycle, nitro, cyano, and unsubstituted or alkyl- or aryl- or heterocycle-substituted hydroxy, thio, amino, amide, formyl (acyl), carboxy, and carboxamide; or R3 and R4 together are alkylene or heteroalkylene attached to adjacent carbons of the phenyl to which R3 and R4 are attached, and R5 is as specified in (e) above;
 (f) R6, R7 and R8 are each independently selected from hydrogen, halo, alkyl, aryl, heterocycle, nitro, cyano, and unsubstituted or alkyl- or aryl- or heterocycle-substituted hydroxy, thio, amino, amide, sulfonamide, formyl (acyl), carboxy, and carboxamide; or R6 and R7 together are alkylene or heteroalkylene attached to adjacent carbons of the phenyl to which R6 and R7 are attached, and R8 is as specified in (f) above;
 (g) R9 is selected from hydrogen, halo, alkyl, aryl, heterocycle, and carboxy and its alkyl and aryl esters and amides;
 (h) R10 and R12, and R11 and R13 if not nil, are each independently selected from hydrogen, alkyl, and aryl;

and an optical isomer, diestereomer or enantiomer thereof; a pharmaccutically acceptable salt, hydrate, or biohydrolyzable ester, amide or imide thereof.

The subject invention also includes compositions comprising a subject compound and a pharmaceutically-acceptable excipient; and methods for treating or preventing diseases or disorders by administering to a human or lower animal in need thereof, a safe and effective amount of a subject compound.

DETAILED DESCRIPTION OF THE INVENTION

As used herein unless specified otherwise, "alkyl" means a hydrocarbon chain which is branched, linear or cyclic, saturated or unsaturated (but not aromatic), substituted or unsubstituted. The term "alkyl" may be used alone or as part of another word where it may be shortened to "alk" (e.g., in alkoxy, alkylacyl). Preferred linear alkyl have from one to about twenty carbon atoms, more preferably from one to about ten carbon atoms, more preferably still from one to about six carbon atoms, still more preferably from one to about four carbon atoms; most preferred are methyl or ethyl. Preferred cyclic and branched alkyl have from three to about twenty carbon atoms, more preferably from three to about ten carbon atoms, more preferably still from three to about seven carbon atoms, still more preferably from three to about five carbon atoms. Preferred cyclic alkyl have one hydrocarbon ring, but may have two, three, or more, fused hydrocarbon rings. Preferred alkyl are unsaturated with from one to about three double or triple bonds, preferably double bonds; more preferably they are mono-unsaturated with one double bond. Still more preferred alkyl are saturated. Saturated alkyl are referred to herein as "alkanyl". Alkyl unsaturated only with one or more double bonds (no triple bonds) are referred to herein as "alkenyl". Preferred substituents of alkyl include halo, alkyl, aryl, heterocycle, hydroxy, alkoxy, aryloxy, thio, alkylthio, arylthio, amino, alkylamino, arylamino, amide, alkylamide, arylamide, fonnyl, alkylacyl, arylacyl, carboxy and its alkyl and aryl esters and amides, nitro, and cyano. Also, unsubstituted alkyl are preferred.

As used herein, "heteroatom" means a nitrogen, oxygen, or sulfur atom.

As used herein, "alkylene" means an alkyl which connects two other moieties, "heteroalkylene" means an alkylene having one or more heteroatoms in the connecting chain.

As used herein unless specified otherwise, "aryl" means an aromatic hydrocarbon ring (or fused rings) which is substituted or unsubstituted. The term "aryl" may be used alone or as part of another word (e.g., in aryloxy, arylacyl). Preferred aryl have from six to about fourteen, preferably to about ten, carbon atoms in the aromatic ring(s), and a total of from about six to about twenty, preferably to about twelve, carbon atoms. Preferred aryl is phenyl or naphthyl; most preferred is phenyl. Preferred substituents of aryl include halo, alkyl, aryl, heterocycle, hydroxy, alkoxy, aryloxy, thio, alkylthio, arylthio, amino, alkylamino, arylamino, amide, alkylamide, arylamide, formyl, alkylacyl, arylacyl, carboxy and its alkyl and aryl esters and amides, nitro, and cyano. Also, unsubstituted aryl are preferred.

As used herein unless specified otherwise, "heterocycle" means a saturated, unsaturated or aromatic cyclic hydrocarbon ring (or fused rings) with one or more heteroatoms in the hydrocarbon ring(s). Preferred heterocycles have from one to about six heteroatoms in the ring(s), more preferably one or two or three heteroatoms in the ring(s). Preferred heterocycles have from three to about fourteen, preferably to about ten, carbon plus heteroatoms in the ring(s), more preferably from three to about seven, more preferably still five or six, carbon plus heteroatoms in the rings(s); and a total of from three to about twenty carbon plus heteroatoms, more preferably from three to about ten, more preferably still five or six, carbon plus heteroatoms. Preferred heterocycles have one ring, but may have two, three, or more, fused rings. More preferred heterocycle rings include those which are one ring with 5 or 6 carbon plus heteroatoms in the ring with no more than three ring heteroatoms, no more than two of which are O and S. Still more preferred are such 5- or 6-ring atom heterocycles with one or two ring atoms being O or S and the others being C; or with one, two or three ring atoms being N and the others being C. Such preferred 5- or 6-ring atom heterocycles are preferably saturated, unsaturated with one or two double bonds, or aromatic. Such preferred 5- or 6-ring atom heterocycles are preferably a single ring; or fused with a 3- to 6-ring atom hydrocarbon ring which is saturated, unsaturated with one double bond, or aromatic (phenyl); or fused with another such 5- or 6-ring atom heterocyclic ring. Heterocycles are unsubstituted or substituted. Preferred heterocycle substituents are the same as for alkyl.

COMPOUNDS OF THE INVENTION

The subject invention involves compounds having the following structure:

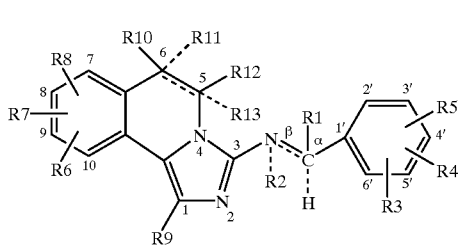

(1)

In structure 1, the bond between the α carbon and the β nitrogen can be either a single bond, in which case R2 and the H attached to the α carbon exist, or a double bond, in which case R2 and that H do not exist (are nil). This $C_\alpha$—$N_\beta$ bond is preferably a single bond.

In structure 1, the bond between carbons 5 and 6 can be either a single bond, in which case R11 and R13 exist, or a double bond, in which case R11 and R13 do not exist (are nil). This $C_5$–$C_6$ bond is preferably a single bond.

In structure 1, R1 is selected from alkyl, aryl, and heterocycle. Preferred R1 include linear alkanyl having from 1 to about 10 carbon atoms, linear alkenyl having from 2 to about 10 carbon atoms, and branched and cyclic alkanyl and alkenyl having from 3 to about 10 carbon atoms, such alkenyl preferably having 1 double bond. Such preferred alkanyl and alkenyl are preferably unsubstituted, or substituted with phenyl, heterocycle having 5 or 6 ring atoms, carboxy and its $C_1$–$C_6$ alkyl and phenyl esters, or cyano. More preferably such alkanyl and alkenyl have up to about 7 carbon atoms, more preferably still up to 6 carbon atoms, still more preferably up to 4 carbon atoms. Most preferred R1 is unsubstituted methyl.

In structure 1, R2, if it exists, is selected from hydrogen, alkyl, alkylacyl, arylacyl, alkylsulfonyl, and arylsulfonyl. Preferred R2 is selected from hydrogen; $C_1$–$C_6$ alkyl, such alkyl being saturated or unsaturated with one double bond and unsubstituted or substituted with phenyl; $C_1$–$C_6$ alkylacyl, the alkyl portion being saturated or unsaturated with one double bond; and phenylacyl. More preferred is the alkyl portions of the aforementioned moieties being $C_1$–$C_4$ and saturated. More preferred still is R2 being methyl. Most preferred R2 is hydrogen.

In structure 1, R3, R4 and R5 are each independently selected from hydrogen, halo, alkyl, aryl, heterocycle, nitro and cyano; also from hydroxy, thio, amino, amide, formyl (acyl), carboxy, and carboxamide which are unsubstituted or substituted, preferably with alkyl or aryl or heterocycle; or R3 and R4 together are alkylene or heteroalkylene attached to adjacent carbon atoms of the phenyl ring, thereby forming a cycloalkyl or aryl or heterocycle ring which is fused to the phenyl ring (phenyl of carbons 1'–6'), and R5 is as defined above. Preferred R3, R4 and R5 are selected from hydrogen, halo, alkyl, aryl, heterocycle, hydroxy, alkoxy, aryloxy, thio, alkylthio, arylthio, amino, alkylamino, arylamino, amide, alkylamide, arylamide, formyl, alkylacyl, arylacyl, carboxy and its alkyl or aryl esters and amides; more preferably from hydrogen, halo, alkyl, alkoxy, phenoxy, thio, alkylthio, phenylthio, mono or dialkylamino, mono- or diphenylamino, alkylacyl, and phenylacyl. Alkyl portions of such substituents are preferably about $C_1$–$C_6$, more preferably about $C_1$–$C_4$, more preferably still methyl or ethyl. Alkyl and phenyl R3, R4 or R5 substituents or portions of such substituents are preferably unsubstituted or substituted with from 1 to about 3 fluoro, more preferably unsubstituted. More preferred is for from one to three of R3, R4, and R5 being halo, the other(s) being hydrogen. Also more preferred is for from one to three of R3, R4 and R5 being methyl or ethyl, the other(s) being hydrogen. Also preferred is R3 being dialkylamino, and R4 and R5 being hydrogen, R3 preferably being attached to the 4' carbon. More preferred still is for from one to three of R3, R4 and R5 being independently selected from F, Cl and Br, the other(s) being hydrogen; still more preferred, when two or three of R3, R4 and R5 are F, Cl or Br, they are the same. Also more preferred is from one to three of R3, R4 and R5 being unsubstituted methyl, the other(s) being hydrogen. Also more preferred is one or two of R3, R4 and R5 being trifluoromethyl, the other(s) being hydrogen or halo, and if halo, preferably fluoro. Also more preferred is one or two of R3, R4 and R5 being methoxy or trifluoromethoxy, the others being hydrogen or halo, and if halo, preferably fluoro.

Also preferred are R3 and R4, which are attached to adjacent carbon atoms of the phenyl ring, together being a saturated or unsaturated alkylene or heteroalkylene having from 1 to about 6 carbon atoms and from 0 to about 3 heteroatoms, thus forming a ring fused to the phenyl, such ring having from about 5 to about 8 ring atoms. Such ring fused to the phenyl preferably has from about 5 to about 6 ring atoms of which from 0 to 2, more preferably 0 or 1, are heteroatoms. Preferred fused rings (including the phenyl to which R3 and R4 are attached) include naphthyl, indolyl, benzimidazoyl, benzofuryl, benzopyranyl. When R3 and R4 form a ring fused with the phenyl, R5 is preferably H.

In structure 1, R6, R7 and R8 are each independently selected from hydrogen, halo, alkyl, aryl, heterocycle, cyano and nitro; also from hydroxy, thio, amino, amide, formyl (acyl), carboxy, carboxamide, and sulfonamide which are unsubstituted or substituted, preferably with alkyl or aryl or heterocycle; or R6 and R7 together are alkylene or heteroalkylene attached to adjacent carbon atoms of the phenyl ring, thereby forming a cycloalkyl or aryl or heterocycle ring which is fused to the phenyl ring (phenyl of carbons 7–10), and R8 is as defined above. Preferred R6, R7 and R8 are selected from hydrogen, halo, alkyl, aryl, heterocycle, hydroxy, alkoxy, aryloxy, thio, alkylthio, arylthio, amino, alkylamino, arylamino, amide, alkylamide, arylamide, sulfonamide, alkylsulfonamide, arylsulfonamide, formyl, alkylacyl, arylacyl, carboxy and its alkyl and aryl esters and amides; more preferably from hydrogen, halo, hydroxy, $C_1-C_4$ alkoxy, thio, $C_1-C_4$ alkylthio, $C_1-C_4$ alkyl esters and amides of carboxy, and heterocycle having 5 or 6 ring atoms. More preferably one or two of R6, R7 and R8 are selected such that at least one heteroatom is bonded directly to the phenyl ring. When two heteroatoms are bonded directly to different carbons, preferably adjacent carbons, of the phenyl ring, those heteroatoms may be connected by an alkylene moiety, the alkylene moiety preferably having from 1 to about 4, more preferably 1 or 2, carbon atoms. Preferred is for one or two of R6, R7 and R8 being non-hydrogen moieties bonded to the fused rings at carbons 8 and/or 9 (as in structure 2 below); more preferred is that two of them be non-hydrogen moieties bonded to carbons 8 and 9. More preferred still is that R8 is hydrogen and that R6 and R7 are both alkoxy or both alkylthio bonded to carbons 8 and 9, respectively; preferably both R6 and R7 are the same. Preferred alkyl portions of R6 and R7 have from 1 to about 4 carbon atoms, more preferably 1 or 2 carbon atoms; most preferred is methyl. Such alkyl portions are preferably unsubstituted. Such alkyl portions are preferably saturated. Most preferred is that both R6 and R7 are methoxy bonded to carbons 8 and 9, R8 being hydrogen.

Also preferred are R6 and R7, which are attached to adjacent carbon atoms of the phenyl ring, together being a saturated or unsaturated alkylene or heteroalkylene having from 1 to about 6 carbon atoms and from 0 to about 3 heteroatoms, thus forming a ring fused to the phenyl, such ring having from about 5 to about 8 ring atoms. Such ring fused to the phenyl preferably has from about 5 to about 6 ring atoms of which from 0 to 2, more preferably 0 or 1, are heteroatoms. Preferred rings formed by R6 and R7 include phenyl, furyl, pyrrolyl, dioxanyl, imidazoyl, pyridinyl, pyrrolidinyl, piperidinyl. When R6 and R7 form a fused ring, R8 is preferably H.

In structure 1, R9 is selected from hydrogen, halo, alkyl, aryl, heterocycle, carboxy and its alkyl esters and amides. Preferred R9 is selected from hydrogen, halo, $C_1-C_4$ alkyl, phenyl. More preferred R9 is selected from hydrogen and unsubstituted and substituted phenyl; substituents on such phenyl are preferably selected from hydroxy, alkoxy, thio and alkylthio. Most preferred R9 is hydrogen.

In structure 1, R10 and R12, and R11 and R13 if they exist, are each independently selected from hydrogen, alkyl and aryl. Preferred R10 and R12, and R11 and R13 if they exist, are selected from hydrogen and alkyl having from 1 to about 4 carbon atoms, especially unsubstituted methyl or ethyl. Most preferred is for R10 and R12, and R11 and R13 if they exist, to all be hydrogen.

The subject invention includes optical isomers, diastereomers, and enantiomers of the compounds of structure 1. The subject invention includes pharmaceutically-acceptable salts, hydrates, and biohydrolizable esters, amides and imides of such compounds.

A "pharmaccutically-acceptable salt" is a cationic salt formed at any acidic group (e.g., carboxy group), or an anionic salt formed at any basic group (e.g., amino group) on a compound of structure 1. Many pharmaceutically-acceptable salts are known. Preferred cationic salts include the alkali metal salts, such as sodium and potassium, alkaline earth metal salts, such as magnesium and calcium, and organic salts, such as ammonium. Preferred anionic salts include halides, sulfonates, carboxolates, phosphates, and the like. Salts of addition may provide an optical center where once there was none.

The compounds of the subject invention, and salts thereof, may have one or more chiral centers. The invention includes all optical isomers of the compounds of structure 1 and salts thereof, including diastereomers and enanteomers The subject invention includes and contemplates each optical isomer, diastereomer or enanteomer thereof, in purified form, substantially purified form, and mixtures, including racemic mixtures.

For compounds of structure 1 having a single $C_\alpha-N_\beta$ bond and different R1 and R2 moieties, the $\alpha$ carbon is stereogenic. For such compounds, those having the R stereoscopic configuration are generally preferred over those having the S configuration.

Preferred compounds of the subject invention include those having structure 2:

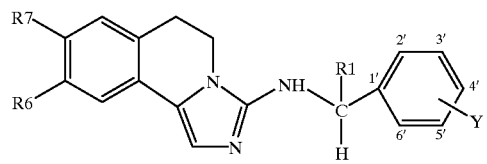

(2)

in structure 2, R1, R6, and R7 are as described hereinabove, and Y is the combinations of R3, R4 and R5 described hereinabove.

In structure 2, R1 is preferably selected from linear alkanyl having from one to four carbon atoms, linear alkenyl having one double bond and from two to four carbon atoms, branched and cyclic alkanyl having from three to five carbon atoms, and branched and cyclic alkenyl having one double bond and from three to five carbon atoms. Such preferred R1 are unsubstituted or substituted with one phenyl, more preferably are unsubstituted. More preferred R1 is selected from methyl, ethyl, ethenyl, n-propyl, i-propyl, n-propenyl, i-propenyl, s-butyl, cyclopropyl, cyclobutyl, and cyclopentyl. More preferred still R1 is selected from methyl, ethyl, ethenyl, i-propyl, and n-propenyl. Most preferred R1 is methyl.

In structure 2, one or both of R6 and R7, preferably both, are preferably alkylthio or more preferably alkoxy with alkanyl having from one to four carbon atoms. If one of R6 and R7 is not alkylthio or alkoxy, it is preferably hydrogen. More preferred is both R6 and R7 being methoxy or ethoxy; most preferred is both R6 and R7 being methoxy.

In structure 2, Y is preferably selected from all hydrogen; mono-, di-, or trihalo, preferably selected from fluoro, chloro and bromo, preferably in one or more of the 2', 3', 4' and 5' positions; mono- di-, and trimethyl, preferably in one or more of the 2', 3', 4' and 6' positions; and mono- or di-trifluoromethyl, preferably in one or both of the 3' and 5' positions. Also preferred is Y being diakylamino, preferably in the 4' position, the two alkyls preferably being the same and preferably having from 1 to 4 carbon atoms. More preferred Y is selected from 4'-fluoro, 4'-chloro, 4'-bromo, 2',4'-difluoro, 2',4'-dichloro, 2',4'-dibromo, 2',4',5'-trifluoro, 2',4',5'-trichloro, 3',4'-difluoro, 3',4'-dichloro, 3',4'-dibromo, 4'-methyl, 2',4'-dimethyl, 2',4',6'-trimethyl 3'-trifluoromethyl, 3',5'-di-trifluoromethyl, and 4'-dibutylamino. Also preferred Y is selected from 2',4'- dihalo and 3',4'-dihalo, where one halo is selected from fluoro, chloro, and bromo, and the other halo is a different one of those three; more preferably one of such halo is fluoro. Most preferred Y is selected from 4'-cholor, 4'-bromo, and 2',4'-dichloro.

Non-limiting examples of compounds of the subject invention include those of structure 2 wherein R6 and R7 are both methoxy, and R1 and Y are as indicated in the following table:

| Example | R1 | Y |
| --- | --- | --- |
| 1 | methyl | hydrogen |
| 2 | methyl | 4'-fluoro |
| 3 | methyl | 4'-chloro |
| 4 | methyl | 4'-bromo |
| 5 | methyl | 2',4'-difluoro |
| 6 | methyl | 2',4'-dichloro |
| 7 | methyl | 2'-fluoro, 4'-chloro |
| 8 | methyl | 2'-fluoro, 4'-bromo |
| 9 | methyl | 2'-chloro, 4'-fluoro |
| 10 | methyl | 2'-bromo, 4'-fluoro |
| 11 | methyl | 3',4'-difluoro |
| 12 | methyl | 3',4'-dichloro |
| 13 | methyl | 3'-fluoro, 4'-chloro |
| 14 | methyl | 3'-fluoro, 4'-bromo |
| 15 | methyl | 3'-chloro, 4'-fluoro |
| 16 | methyl | 3'-bromo, 4'-fluoro |
| 17 | methyl | 2',4',5'-trifluoro |
| 18 | methyl | 4'-methyl |
| 19 | methyl | 2',4'-dimethyl |
| 20 | methyl | 3',4'-dimethyl |
| 21 | methyl | 2',4',6'-trimethyl |
| 22 | methyl | 3'-trifluoromethyl |
| 23 | methyl | 3',5'-di-trifluoromethyl |
| 24 | methyl | 4'-fluoro,3'-trifluoromethyl |
| 25 | ethyl | 4'-fluoro |
| 26 | ethyl | 4'-chloro |
| 27 | ethyl | 4'-bromo |
| 28 | ethyl | 2',4'-dichloro |
| 29 | ethyl | 3'-fluoro, 4'-chloro |
| 30 | ethenyl | 4'-chloro |
| 31 | ethenyl | 2',4'-dichloro |
| 32 | i-propyl | 4'-fluoro |
| 33 | i-propyl | 4'-chloro |
| 34 | i-propyl | 4'-bromo |
| 35 | i-propyl | 2',4'-dichloro |
| 36 | i-propyl | 3'-fluoro, 4'-chloro |
| 37 | —CH$_2$—CH=CH$_2$ | 4'-fluoro |
| 38 | —CH$_2$—CH=CH$_2$ | 4'-chloro |
| 39 | —CH$_2$—CH=CH$_2$ | 2',4'-dichloro |
| 40 | s-butyl | 4'-chloro |
| 41 | cyclopentyl | 4'-chloro |
| 42 | methyl | 2',4',5'-trifluoro |
| 43 | methyl | 2',3',4'-trifluoro |
| 44 | ethyl | 2',4',5'-trifluoro |
| 45 | ethyl | 2',3',4'-trifluoro |
| 46 | i-propyl | 2',4',5'-trifluoro |
| 47 | i-propyl | 2',3',4'-trifluoro |
| 48 | methyl | 4'-dibutylamino |
| 49 | ethyl | 4'-dimethylamino |
| 50 | i-propyl | 4'-diethylamino |
| 51 | cyclohexyl | 4'-fluoro |
| 52 | s-butyl | 4'-fluoro |
| 53 | methyl | 3'-methyl |
| 54 | s-butyl | all hydrogen |
| 55 | s-butyl | n-propoxy |
| 56 | s-butyl | 2',3'-dimethoxy |
| 57 | s-butyl | 4'-phenoxy |
| 58 | s-butyl | 3'-trifuoromethoxy |
| 59 | s-butyl | 3'-methoxy, 4'-hydroxy |
| 60 | s-butyl | 2'-fluoro |
| 61 | n-hexyl | 3-(dimethylamino)propoxy |
| 62 | n-hexyl | 4'-i-propyl |
| 63 | n-hexyl | 4'-t-butoxy |
| 64 | n-hexyl | 1',5'-dimethyl-4'-methoxy |
| 65 | n-hexyl | 4'-trifluoromethyl |

-continued

| Example | R1 | Y |
| --- | --- | --- |
| 66 | n-hexyl | 2'-methyl |
| 67 | n-hexyl | 3',4'-dichloro |
| 68 | s-butyl | 1'-naphthyl |
| 69 | s-butyl | 4'-dimethylamino-1'-naphthyl |

In addition, it is recognized that for purification, administration, and the like, the salts and other derivatives of the above compounds can be used. Thus a pharmaceutically-acceptable salt, hydrate, or biohydrolizable ester, amide or imide therefore is contemplated as part of the subject invention.

METHODS OF MAKING THE COMPOUNDS

In making the compounds of the subject invention, the order of synthetic steps may be varied to increase yield of desired product. The skilled artisan will recognize that the judicious choice of reactants, solvents, and temperatures is important in successful synthesis. The starting materials used in preparing the subject compounds are known, made by known methods, or are commercially available.

It is recognized that the skilled artisan can readily carry out standard manipulations of organic compounds without further direction. These include, but are not limited to, reduction, oxidation, acylation, substitution, etherification, esterification, sulfonation, and the like. Examples of these manipulations are discussed in standard texts.

Procedures for preparing some imidazo-isoquinoline compounds are disclosed in U.S. Pat. No. 3,917,610 issued Nov. 4, 1975, and U.S. Pat. No. 4,143,143 issued on Mar. 6, 1979, both of which are incorporated herein by reference.

The following general schemes can be used for synthesizing compounds of the subject invention.

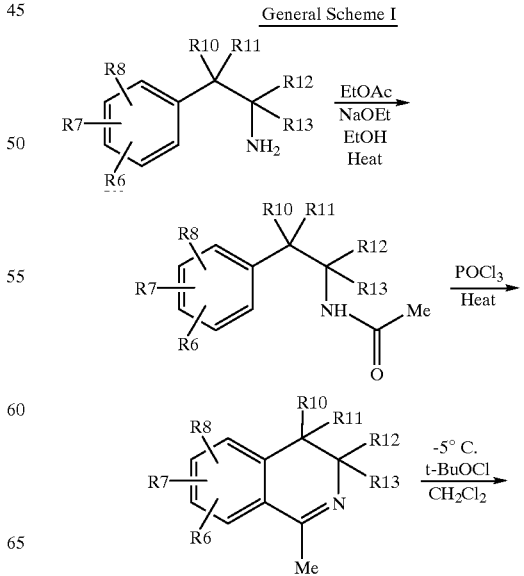

General Scheme I

9
-continued
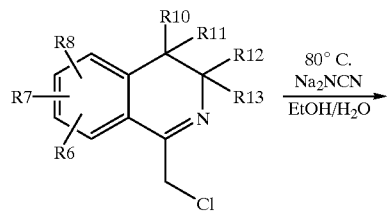
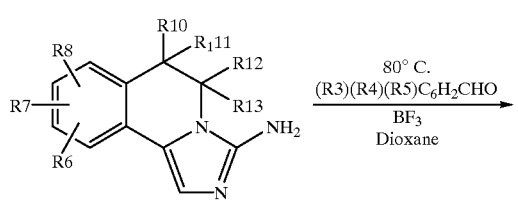
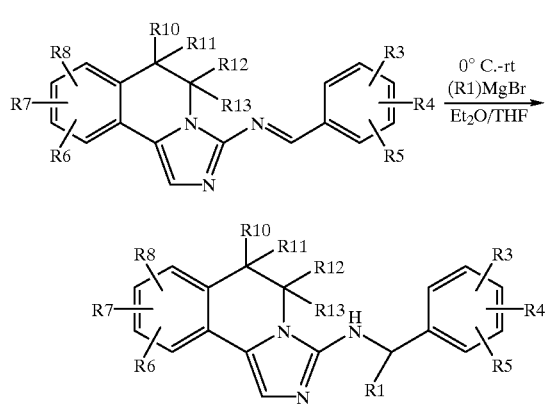
General Scheme II
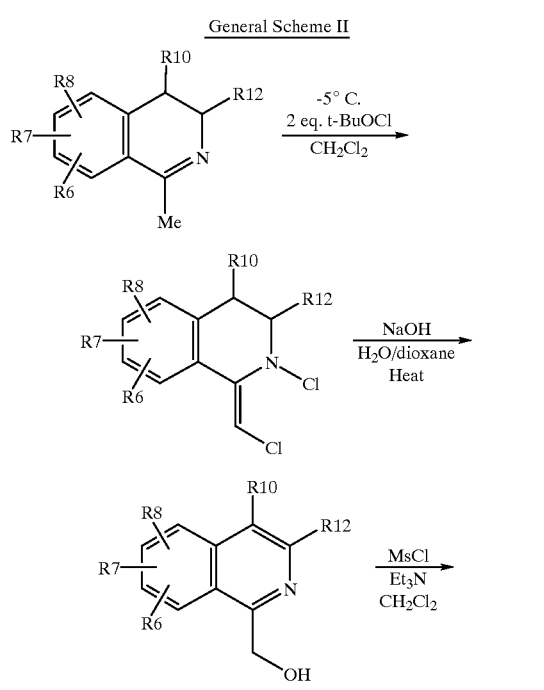
10
-continued
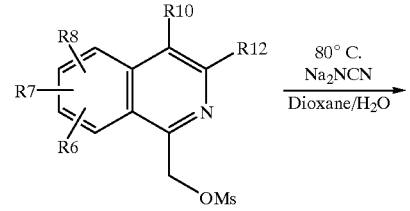
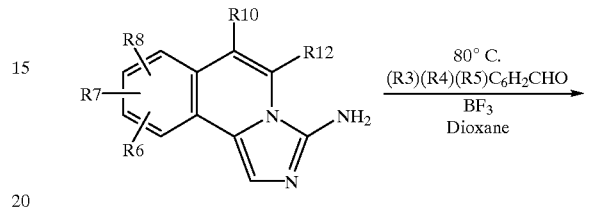
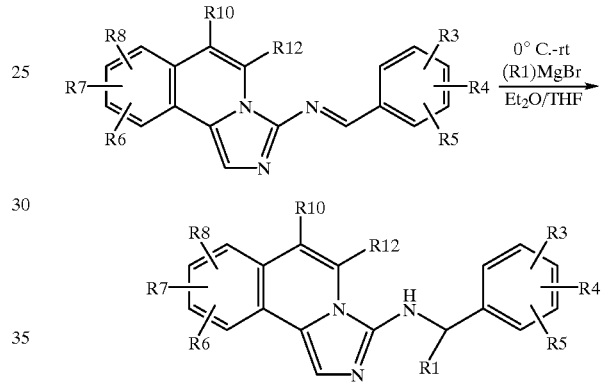
General Scheme III
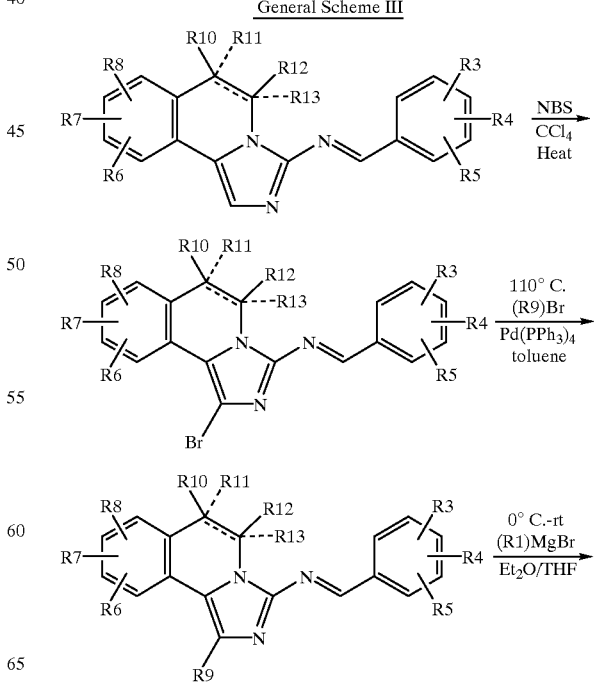

-continued

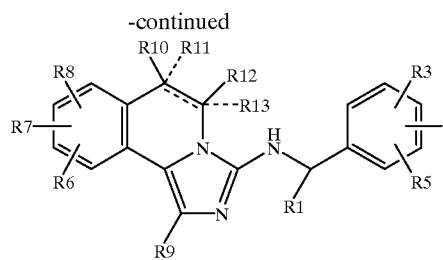

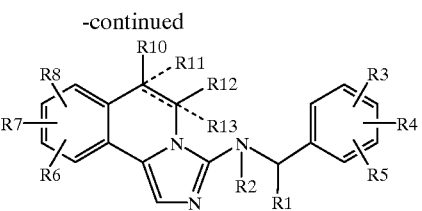

The following examples provide further information regarding synthesis of the subject invention compounds:

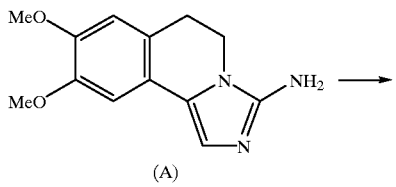

(A)

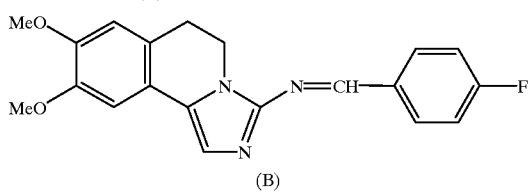

(B)

General Scheme IV

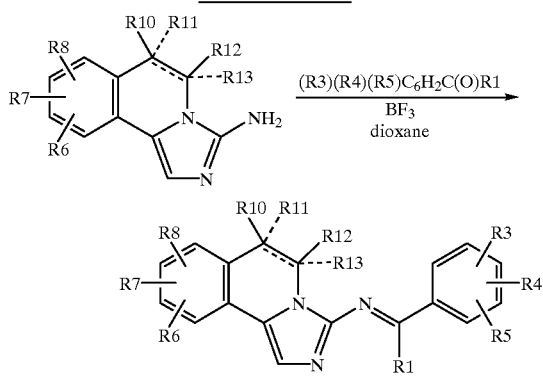

General Scheme V

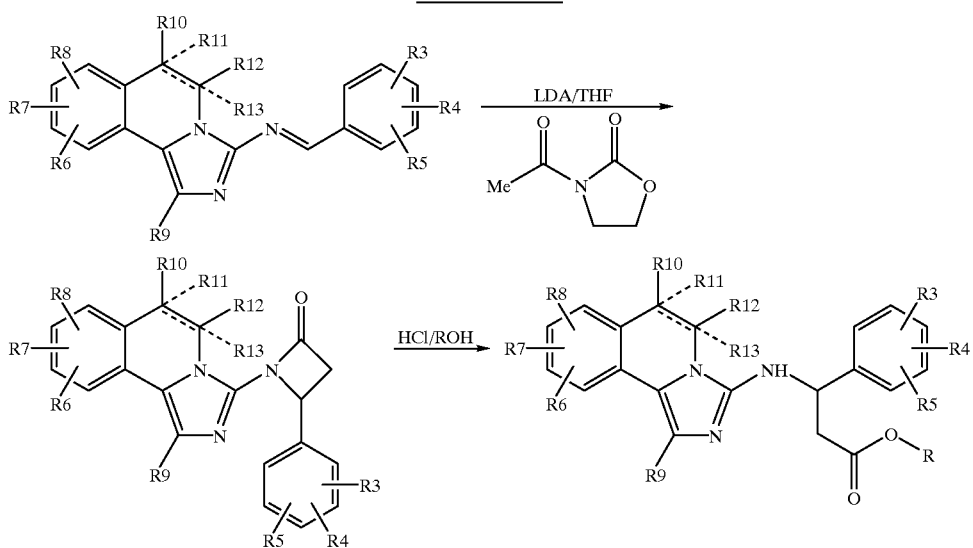

General Scheme VI

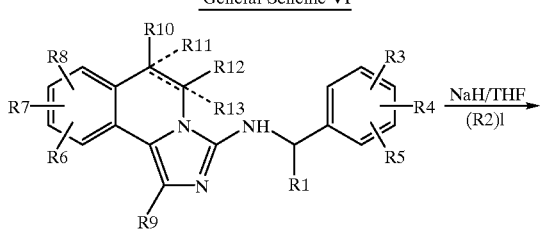

Benzyl-imine B. Method 1: A mixture of compound A (808 mg, 3.3 mmol) and 4-F-benzaldehyde (10 mmol) in 35 mL of absolute EtOH is refluxed for 14 h. (For substituted benzaldehydes that are not reactive enough, molecular sieves can be added to drive the reaction by removing $H_2O$) Evaporation of the solvent and chromatography of the resultant residue provides purified imine B.

Benzyl-imine B. Method 2: To a solution of compound A (1 mmol) and 4-F-benzaldehyde (3 mmol) in 10 mL of anhydrous 1,4-dioxane, $BF_3$-$Et_2O$ (3 drops) is added. The mixture is heated to 80° C. under nitrogen for 2 h. (More $BF_3$-$Et_2O$ can be added if needed to drive the reaction to completion.) The solvent is thoroughly evaporated to give a crude residue which is partitioned in $CH_2Cl_2$ and 5% aqueous $NaHCO_3$ (2:1). The separated aqueous layer is extracted with $CH_2Cl_2$. The combined extracts are washed with brine and dried over $Na_2SO_4$. Purification of the crude product by chromatography gives purified imine B.

Method 2 can be used to obtain good yield with benzaldehydes having variety of substituents of different electronic and steric properties. Method 1 often does not work well when the benzaldehydes have electron donating substituent groups.

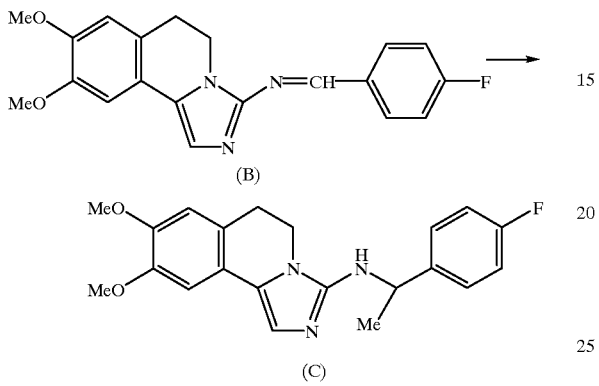

N-1-phenylethyl-imidazoisoquinoline-3-amine C. MeMgBr (2.8M concentration, 1.2 mmol) in $Et_2O$ is added dropwise to a solution of B (1 mmol) in 10 mL of anhydrous THF at 0° C. under nitrogen. The mixture is stirred at room temperature for 15 min. TLC ($CH2Cl_2$/MeOH 9:1) is used to monitor the reaction. After completion, ethyl acetate and then MeOH is added to destroy excess Grignard reagent. Concentration of the solution gives a white solid residue which is partitioned in $CH_2Cl_2$/5% aqueous $NaHCO_3$ (1:1). The aqueous layer is extracted with $CH_2Cl_2$. The extracts are washed with 5% aqueous $NaHCO_3$ and brine, and are dried over $Na_2SO_4$. The crude residue after evaporation is purified by chromatography to provide product C.

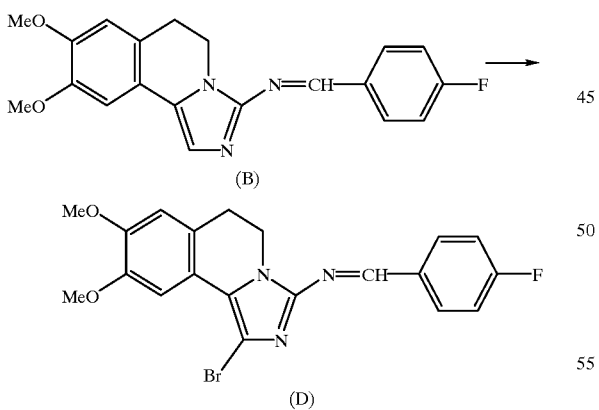

1-Bromination. N-bromosuccinimide (NBS) solid (98 mg, 0.55 mmol) is added to a solution of compound B (0.5 mmol) in 15 mL of $CCl_4$. Radical initiator benzoyl peroxide (2 mol%) is subsequently added. The flask is placed onto a 90° C. oil bath. After 10 min stirring, TLC ($CHCl_3$/MeOH 9:0.3) indicates the reaction is complete. Filtration of the mixture through a celite pad, and evaporation of the filtrate gives a residue. Purification by chromatography affords purified product D.

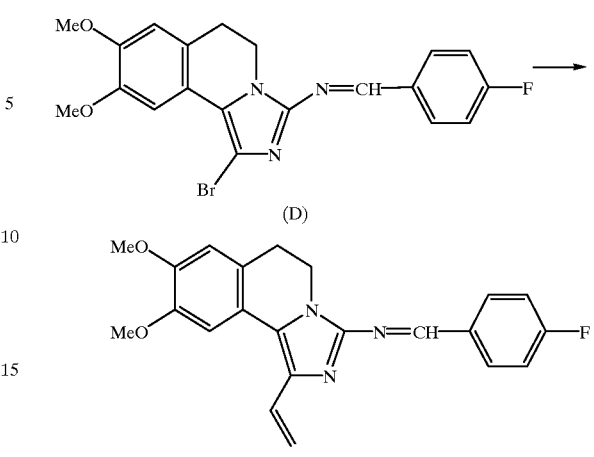

Stille coupling to form E. To a solution of D (0.22 mmol) and $Pd(PPh_3)_4$ (13 mg, 0.056 mmol) in 7 mL of anhydrous toluene are added vinyltributyltin (0.072 mL, 0.26 mmol) and a few crystals of 2,6-di-tert-butyl-4-methylphenol. The reaction mixture is allowed to reflux at 110° C. under nitrogen for 6 hours. Thin-layer chromatography (TLC) using a 9.9:0.1 $CH_2Cl_2$/MeOH eluant system indicates completion of the reaction. The reaction mixture is allowed to cool, and is then diluted with 1–2 mL of ethyl acetate (EtOAc). The resultant mixture is washed with water, then brine, extracted with EtOAc, dried over $Na_2SO_4$, and filtered. The filtrate is treated with 3 mL of 30% aqueous KF at room temperature for 2 h. The light purple-violet solid is filtered off. The filtrate is diluted with EtOAc and washed with water, 30% aqueous $NH_4OH$ (3X), brine, extracted with EtOAc, dried ($Na_2SO_4$), and concentrated in vacuo to yield crude product. Chromatography (silica gel) with a gradient elution system of $CH_2Cl_2$ and 9.7:0.3 $CH_2Cl_2$/MeOH yields product E.

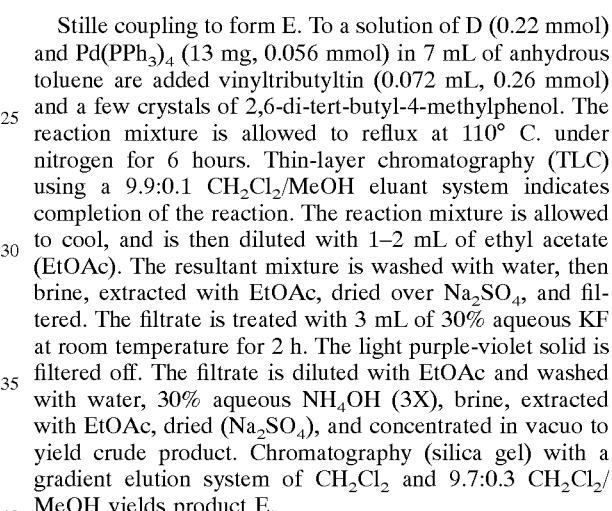

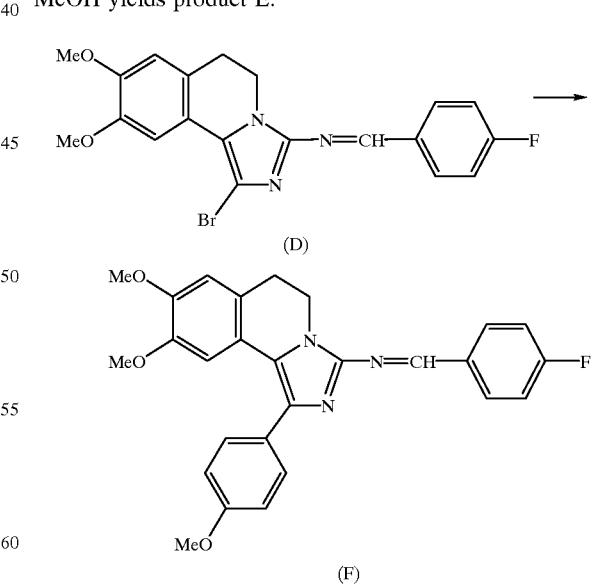

Suzuki coupling to form F. To a solution of D (500 mg, 1.1 mmol) and $Pd(PPh_3)_4$ (76 mg, 0.066 mmol) in 25 mL of distilled xylene is added 1.1 mL of 2M $Na_2CO_3$. The reaction mixture is placed under nitrogen; the system is heated to completely dissolve the starting material. A boronic acid solution is prepared by dissolving 4-methoxybenzeneboronic acid (334 mg, 2.2 mmol) in 2 mL of hot absolute ethanol. The boronic acid solution is added dropwise to the refluxing reaction mixture over the course of 2 h. The reaction mixture is allowed to reflux for 21 hours, and is then cooled. The catalyst is removed by filtration through a celite pad. The filtrate is concentrated on a high vacuum rotovapor apparatus. The residual is partitioned in 1:1 $CH_2Cl_2$/brine, extracted with $CH_2Cl_2$, dried over $Na_2SO_4$, and filtered over $Na_2SO_4$. The filtrate is concentrated in vacuo to yield crude product, and chromatography (silica gel) with 2.5:7.5 ethyl acetate/hexane yields F as an orange solid.

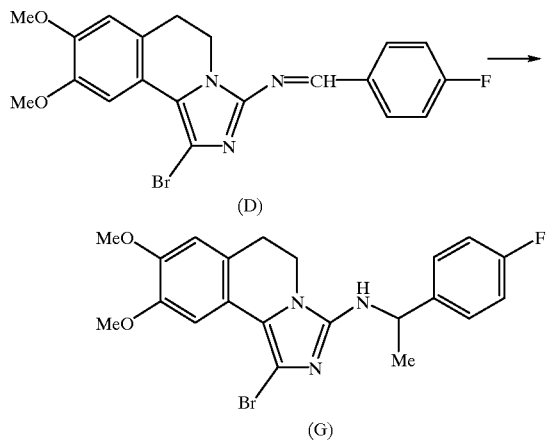

N-1-phenylethyl-1-bromo-imidazoisoquinoline-3-amine G. MeMgBr (2.8M concentration, 1.2 mmol) in $Et_2O$ is added dropwise to a solution of D (1 mmol) in 10 mL of anhydrous THF at 0° C. under nitrogen. The mixture is stirred at room temperature for 15 min. TLC ($CH_2C_{12}$/ MeOH 9:1) is used to monitor the reaction.

After completion, ethyl acetate and then MeOH are added to destroy excess Grignard reagent. Concentration of the solution gives a white solid residue which is partitioned in $CH_2Cl_2$/5% aqueous $NaHCO_3$ (1:1). The aqueous layer is extracted with $CH_2Cl_2$. The extracts are washed with 5% aqueous $NaHCO_3$ and brine, and are dried over $Na_2SO_4$. The crude residue after evaporation is purified by chromatography to provide product G.

EXAMPLE H

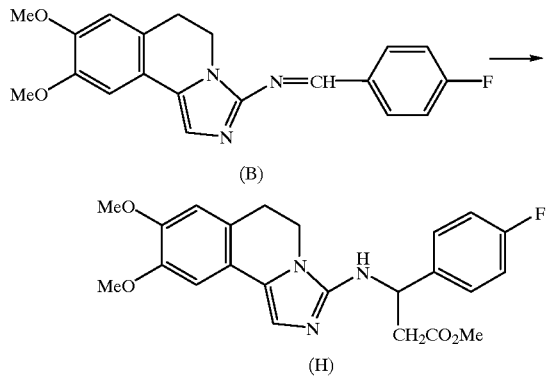

N-[3-(4-Fluorophenyl)methylpropionate]-5,6-dihydro-8, 9-dimethoxyimid-azo[5,1-a] isoquinolin-3-amine H. To a solution of lithium diisopropylamine (LDA) (2.0 ml, 3.0 mmol) in THF (5 ml) under nitrogen at −78° C., N-acetyl-2-oxazolidinone (0.323 g, 2.5 mmol) in THF (3 ml) is added dropwise. The mixture is warmed to −15° C. for 1 h and cooled again to −78° C. Compound B (0.44 g, 1.25 mmol) in THF (3 ml) is added dropwise, and the mixture is stirred at −78° C. for 2 h (monitored by TLC, $CH_2Cl_2$/MeOH 9:1). The reaction is quenched by adding 1N HCl in MeOH, and the solvent is removed in vacuum. The residue is partitioned in $CH_2Cl_2$/5% $NaHCO_3$ and the organic phase was washed with 5% $NaHCO_3$, brine, dried over $MgSO_4$, and evaporated. Chromatography ($CH_2Cl_2$/MeOH, 9.7:0.3) gives H as a light yellow powder.

EXAMPLE J

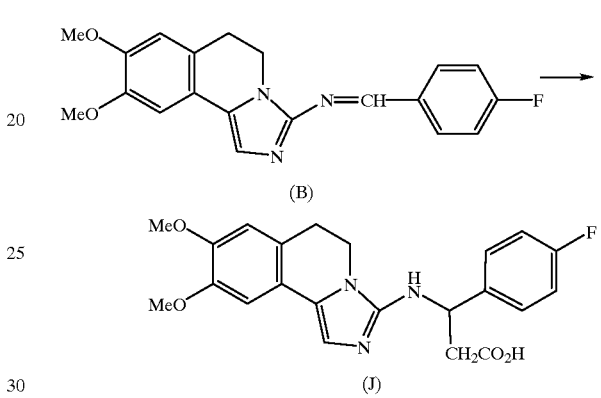

3-(4-Fluorophenyl)-3-[N-9-5,6-dihydro-8,9-dimethoxyimidazo[5,1 -a]isoqui-nolin)]-amino propionic acid hydrochloride J. To a solution of LDA (2.0 ml, 3.0 mmol) in dry THF (5 ml) under nitrogen at −78° C., N-acetyl-2-oxazolidinone (0.323 g, 2.5 mmol) in THF (3 ml) is added dropwise. The mixture is warmed to −15° C. for 1 h, and cooled again to −78° C. Compound B (0.44 g, 1.25 mmol) in THF (3 ml) is added dropwise, and the mixture is stirred at −78° C. for 2 h (monitored by TLC, $CH_2Cl_2$/ MeOH, 9:1). The reaction is quenched by adding 1N HCl, and the solvent is removed in vacuum. The residue is partitioned in $CH_2Cl_2$/ 5% $NaHCO_3$, and the organic phase is washed with 5% $NaHCO_3$, brine, dried over $MgSO_4$, and evaporated. Chromatography ($CH_2Cl_2$/MeOH, 9.7:0.3) gives J as a light yellow powder.

EXAMPLE K

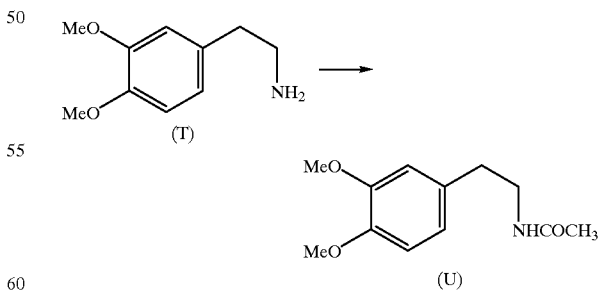

Preparation of the amide U. To NaOEt solution (50 mL) prepared by adding Na (295 mg, 12.8 mmol) into absolute ethanol is added compound T (2.52 g, 12.8 mmol) in ethanol (5 mL). The mixture is stirred for 10 min. Ethyl acetate (10 mL) is added into the solution. The mixture is then refluxed under N₂ for 6 h. After the reaction goes to completion, the solvent is evaporated, and the product is crystallized from EtOH.

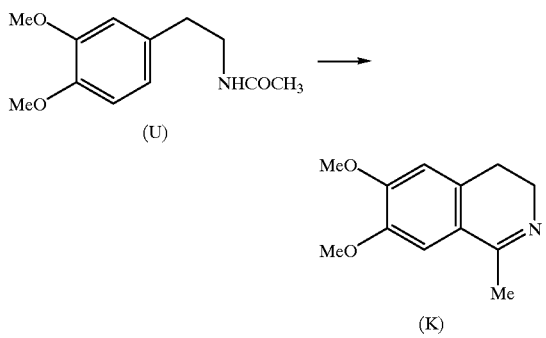

POCl₃ catalyzed cyclization. A suspended mixture of acetyl amide U (1.61 g, 7.0 mmol) in POCl₃ (15 mL) is refluxed for 2 h. The starting material goes into solution as the temperature rises. Evaporation of the solvent under vacuum in hood gives a residue. Toluene is added to this residue to thoroughly remove the POCl₃. The crude product is partitioned with CH₂Cl₂ and H₂O. The aqueous solution is neutralized with NH₄OH and extracted with CH₂Cl₂. The combined organic extracts are washed with brine and dried over Na₂SO₄. Removal of the solvent gives product K. Crystallization is necessary to purify product K.

EXAMPLE L

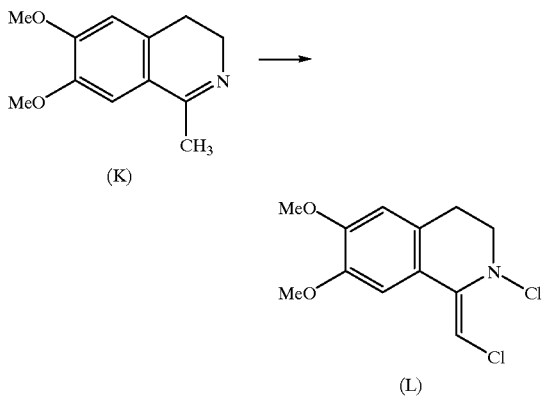

Dichloronation of imine. In a 100 ml single neck round bottom flask, equipped with a magnetic stir bar, rubber septum and nitrogen inlet, is placed 5 g of K [Source?] under nitrogen while 50 ml of CH₂Cl₂ is added. The reaction is cooled to −5° C. using an ice/acetone bath, and 6.78 ml of t-butyl hypochlorite is added dropwise. The reaction is complete in 15 minutes. The reaction product is evaporated in vacuo, and the residue is purified by silica gel chromatography using neat CH₂Cl₂ as eluting solvent. Compound L is obtained from the column.

EXAMPLE M

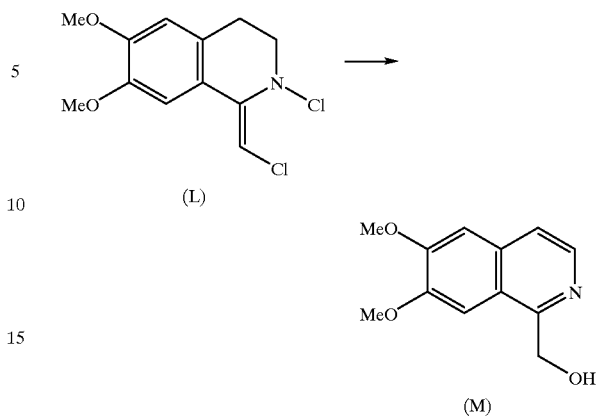

1-Hydroxymethyl-isoquinoline M. In a single neck 50 ml round bottom flask equipped with a magnetic stir bar and water condenser is placed 72 mg of NaOH in 12 ml H₂O. This is heated to reflux; then 500 mg of L is taken up in 10 ml of dioxane and added to the flask. The reaction solution is refluxed for 3 hours and evaporated in vacuo. The resultant residue is purified by chromatography to afford compound M.

EXAMPLE P

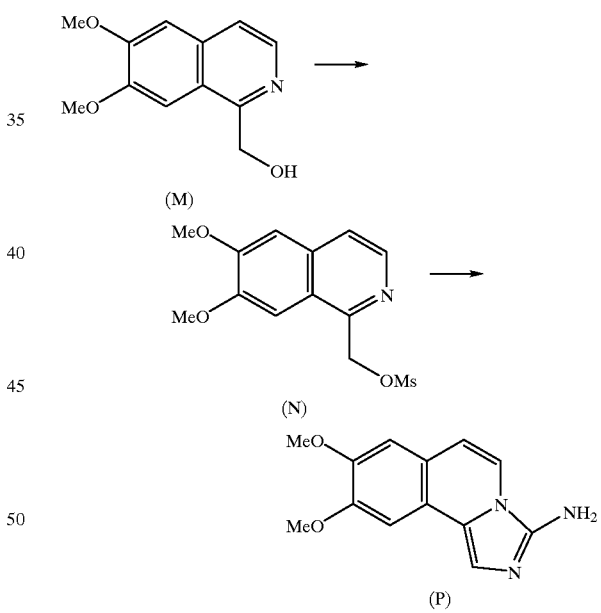

8,9-Dimethoxy-imidazo[5,1-a]isoquinolin-3-amine P. To a solution of compound M in CH₂Cl₂, 1 equivalent of Et₃N is added. After the solution is stirred at room temperature for 5 min, 1 equivalent of methyl-sulfonyl chloride is added dropwise. The reaction is complete in 1 hour. The solution then is diluted with more CH₂Cl₂ and washed with H₂O and brine. The organic layer is separated and dried over Na₂SO₄. Removal of the solvent gives residue N. In a separate flask is placed NaOH solution; then Na₂NCN is added along with EtOH. This is heated to reflux; then residue N is dissolved in EtOH and added to the reaction. After refluxing for 3 hours, the reaction is complete. Removal of the solvent provides a crude product which is purified by silica gel column to give compound P.

EXAMPLE Q

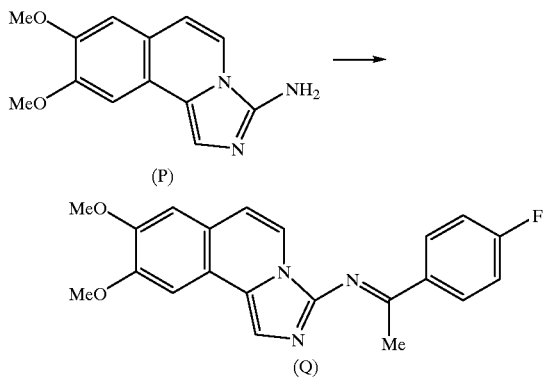

Condensation to form α-methyl-benzyl-imine. Compound P (200 mg, 0.82 mmol) is dissolved in 10 mL dioxane, followed by addition of 4-fluoro-phenylmethylketone (170 mg, 1.23 mmol) and $BF_3$ etherate (20 uL). The mixture is then refluxed for 12 h. Evaporation of the solvent gives a residue. This residue is dissolved in $CH_2Cl_2$, washed with 5% $Na_2CO_3$, and dried over $Na_2SO_4$. The solvent is removed, and the resulting crude product is purified by silica gel chromatography (5% MeOH in $CH_2Cl_2$) to give compound Q.

Similar chemistry is used to prepare compound S from compound A:

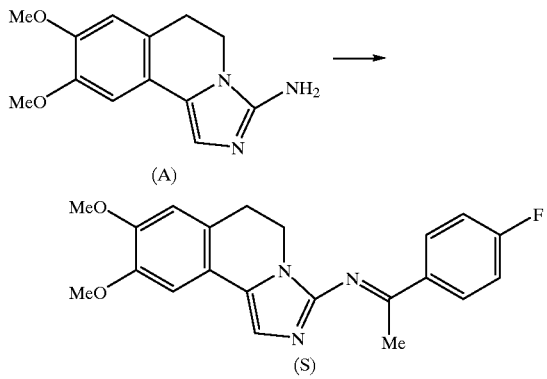

COMPOSITIONS OF THE INVENTION

A composition of the subject invention comprises:
a) a safe and effective amount of a compound of the invention; and
b) a pharmaceutically-acceptable excipient.

Typically, such composition comprises several excipients. It may also optionally comprise other active compounds which do not substantially interfere with the activity of the subject invention compound.

The compositions of the subject invention may be in any of a variety of forms, suitable (for example) for oral, rectal, topical or parenteral administration. Compositions of the subject invention are preferably provided in unit dosage form. As used herein, a "unit dosage form" is a composition containing an amount of a subject compound that is suitable for administration to a human or lower animal subject, in a single dose, according to good medical practice.

As used herein, a "safe and effective amount" of a subject compound is an amount large enough to significantly induce a positive modification in the symptoms and/or condition to be treated in a host, but small enough to avoid serious adverse side effects in the host (such as toxicity, irritation, or allergic response), commensurate with a reasonable benefit/risk ratio. The safe and effective amount will vary with such factors as the particular condition being treated, the age and physical condition of the patient, the duration of treatment, the nature of concurrent therapy (if any), the specific dosage form to be used, and the dosage regimen employed.

The term "pharmaceutically-acceptable excipient", as used herein, includes physiologically inert, pharmacologically inactive substances which are compatible with the physical and chemical characteristics of the subject invention compound used, and which are of sufficiently high purity and sufficiently low toxicity to be suitable for administration to a human or lower animal. The term "compatible", as used herein, means that the excipients of the subject composition are capable of being commingled with the subject invention compound, and with each other in a manner such that there is no interaction which would substantially reduce the pharmaceutical efficacy of the compound, under ordinary use situations.

Depending upon the particular route of administration desired, a variety of pharmaceutically-acceptable excipients well-known in the art may be used. Excipients include, but are not limited to, polymers, resins, plasticizers, fillers, binders, lubricants, glidants, disintegrants, solvents, co-solvents, buffer systems, surfactants, preservatives, sweetening agents, flavoring agents, and dyes or pigments. The amount of excipients employed in conjunction with the subject compound is sufficient to provide a practical quantity of material for administration per unit dose of the subject compound.

Some examples of substances which can serve as pharmaceutically-acceptable excipients are sugars, such as lactose, dextrose, glucose and sucrose; starches, such as cornstarch and potato starch; cellulose and its derivatives, such as methylcellulose, sodium carboxymethylcellulose, ethylcellulose, hydroxypropylcellulose and cellulose acetate; polymers, such as provide and carbomers; powdered tragacanth; gums, such as xanthan, guar and acacia; malt; solid lubricants, such as stearic acid, magnesium stearate, and talc; inorganic fillers, such as calcium phosphates and calcium sulfate; disintigrants, such as sodium starch glycolate, crospovidone, croscarmelose sodium, and microcrystalline cellulose; encapsulating and coating materials, such as gelatins, waxes, and cellulose derivatives; vegetable oils, such as peanut oil, cottonseed oil, sesame oil, olive oil, corn oil and oil of the obroma; polyols such as propylene glycol, glycerin, sorbitol, mannitol, and polyethylene glycol; alginic acid; surfactants such as the Tweens®, alkyl sulfate salts, salts of fatty acids, sucrose esters; ethyl olcate; coloring agents; flavoring agents; tableting agents; stabilizers; antioxidants; preservatives; solvents, such as ethanol, pyrogen-free water; isotonic saline; and buffer solutions, such as phosphoric, tartaric, citric, and acetic acids, and their sodium, potassium, and ammonium salts.

Preferred compositions of the subject invention are oral dosage forms. The term "oral dosage form", as used herein, means any pharmaceutical composition intended to be systemically administered to an individual by delivering the composition via the mouth to the gastrointestinal tract of an individual. Preferred are oral unit dosage forms, such as tablets, coated or non-coated, and capsules, hard or soft gel. Subject oral unit dosage form compositions comprise preferably at least about 4 mg, more preferably at least about 20 mg, more preferably still at least about 100 mg, and preferably at most about 1000 mg, more preferably at most about 500 mg, more preferably still at most about 250 mg, of a subject compound. Subject oral dosage form compositions comprise preferably at least about 1%, more preferably at least about 10%, and preferably at most about 70%, more preferably at most about 40%, of a subject compound; and comprise preferably at least about 30%, more preferably at least about 60%, and preferably at most about 99%, more preferably at most about 90%, pharmaceutically-acceptable excipients.

Parenteral dosage forms are also preferred subject invention compositions. The term "parenteral dosage form", as used herein, means any pharmaceutical composition intended to be systemically administered to a human or lower animal via delivery of a solution or emulsion containing the active ingredient, by puncturing the skin of the individual, in order to deliver the solution or emulsion to the circulatory system of the individual either by intravenous, intramuscular, intraperitoneal or subcutaneous injection. Subject parenteral unit dosage form compositions comprise preferably at least about 1 mg, more preferably at least about 6 mg, more preferably still at least about 30 mg, and preferably at most about 400 mg, more preferably at most about 100 mg, more preferably still at most about 40 mg, of a subject compound. Subject parenteral dosage form compositions comprise preferably at least about 1%, more preferably at least about 5%, and preferably at most about 20%, more preferably at most about 10%, of a subject compound; and comprises preferably at least about 80%, more preferably at least about 90%, and preferably at most about 99%, more preferably at most about 95%, pharmaceutically-acceptable excipients. In addition, dosages for injection may be prepared in dried or lyophilized form. Such forms can be reconstituted with water, saline solution, or a buffer solution, depending on the preparation of the dosage form. Such forms may be packaged as individual dosages or multiple dosages for easier handling. Where lyophilized or dried dosages are used, the reconstituted dosage form is preferably isotonic, and at a physiologically compatible pH, and comprises the subject compound and excipients in the amounts and percentages indicated previously in this paragraph.

METHODS OF TREATMENT USING THE COMPOUNDS

Subject invention compounds have demonstrated pharmacological activity in processes known to be associated with one or more of cardiovascular activity, inflammatory mechanisms, oncology, and regulation of protein transport from cells. The subject invention includes methods of using the above compounds of the subject invention for therapeutic or preventative treatment of one or more of the following diseases or disorders: congestive heart failure, arrhythmia, hypotension, cardiac reperfusion injury, arteriosclerosis, restenosis, vascular tone, bacterial infection, cancer, Kaposi's sarcoma, psoriasis, migraine, nasal congestion, allergic responses, rheumatoid arthritis, and osteoporosis. Such methods comprise administering to a human or lower animal in need of such treatment or prevention a safe and effective amount of a subject invention compound.

For preferred oral administration of compounds and/or compositions of the subject invention, preferably at least about 0.1 mg/kg, more preferably at least about 0.5 mg/kg, more preferably still at least about 2 mg/kg, and preferably at most about 20 mg/kg, more preferably at most about 5 mg/kg, more preferably still at most about 2 mg/kg, of a subject compound is administered to a human or lower animal, preferably at least about 1 time, more preferably at least about 2 times, and preferably at most about 4 times, more preferably at most about 2 times, daily. Treatment duration using such oral daily dosages is dependent on the disease or disorder being treated; it is preferably at least about 1 day, more preferably at least about 3 days, more preferably still at least 7 days, and preferably at most about 5 years, more preferably at most about 60 days, more preferably still at most about 15 days.

For preferred parenteral administration of compounds and/or compositions of the subject invention, preferably at least about 0.04 mg/kg, more preferably at least about 0.2 mg/kg, more preferably still at least about 1 mg/kg, and preferably at most about 10 mg/kg, more preferably at most about 4 mg/kg, more preferably still at most about 1 mg/kg, of a subject compound is administered to a human or lower animal, preferably at least about 1 time, more preferably at least about 2 times, and preferably at most about 4 times, more preferably at most about 2 times, daily. Treatment duration using such parenteral daily dosages is dependent on the disease or disorder being treated; it is preferably at least about 1 day, more preferably at least about 3 days, more preferably still at least 7 days, and preferably at most about 60 days, more preferably at most about 20 days, more preferably still at most about 5 days.

While particular embodiments of the subject invention have been described, it will be obvious to those skilled in the arts that various changes and modifications of the subject invention can be made without departing from the spirit and scope of the invention. It is intended to cover, in the appended claims, all such modifications that are within the scope of this invention.

What is claimed:

1. A compound having the structure:

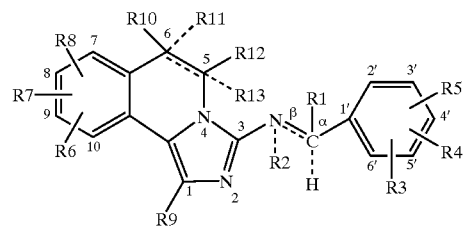

wherein:
(a) The bond between $C_\alpha$ and $N_\beta$ is a single bond, or a double bond whereby R2 (and H on $C_\alpha$) are nil;
(b) the bond between $C_5$ and $C_6$ is a single bond, or a double bond whereby R11 and R13 are nil;
(c) R1 is selected from the group consisting of alkyl, aryl, and heterocycle;
(d) R2, if not nil, is selected from the group consisting of hydrogen, alkyl, alkylacyl, arylacyl, alkylsulfonyl, and arylsulfonyl;
(e) R3, R4 and R5 are each independently selected from the group consisting of hydrogen, halo, alkyl, aryl, heterocycle, nitro, cyano, and unsubstituted or alkyl- or aryl- or heterocycle-substituted hydroxy, thio, amino, amide, formyl (acyl), carboxy, and carboxamide; or R3 and R4 together are alkylene or heteroalkylene attached to adjacent carbons of the phenyl to which R3 and R4 are attached, and R5 is as specified in (e) above;

(f) R6, R7 and R8 are each independently selected from the group consisting of hydrogen, halo, alkyl, aryl, heterocycle, nitro, cyano, and unsubstituted or alkyl- or aryl- or heterocycle-substituted hydroxy, thio, amino, amide, sulfonamide, formyl (acyl), carboxy, and carboxamide; or R6 and R7 together are alkylene or heteroalkylene attached to adjacent carbons of the phenyl to which R6 and R7 are attached, and R8 is as specified in (f) above;

(g) R9 is selected from the group consisting of hydrogen, halo, alkyl, aryl, heterocycle, and carboxy and its alkyl and aryl esters and amides;

(h) R10 and R12, and R11 and R13 if not nil, are each independently selected from the group consisting of hydrogen, alkyl, and aryl;

and an optical isomer, diastereomer or enantiomer thereof; a pharmaceutically acceptable salt, hydrate, or biohydrolyzable ester, amide or imide thereof.

2. The compound of claim 1 wherein:

(a) R1 is selected from the group consisting of linear, branched and cyclic alkanyl and alkenyl, and phenyl;

(b) R2, if not nil, is selected from the group consisting of hydrogen; linear, branched and cyclic alkanyl and alkenyl; alkylacyl; and phenylacyl;

(c) R3, R4, and R5 are each independently selected from the group consisting of hydrogen, halo, alkyl, aryl, heterocycle, hydroxy, alkoxy, aryloxy, thio, alkylthio, arylthio, amino, alkylamino, arylamino, amide, alkylamide, arylamide, formyl, alkylacyl, arylacyl, carboxy and its alkyl and aryl esters and amides; or R3 and R4 together are alkylene or heteroalkylene and, with the carbons to which they are attached, are a cycloalkyl, aryl or heterocycle ring, and R5 is hydrogen; and (d) R6, R7, and R8 are each independently selected from the group consisting of hydrogen, halo, alkyl, aryl, heterocycle, hydroxy, alkoxy, aryloxy, thio, alkylthio, arylthio, amino, alkylamino, arylamino, amide, alkylamide, arylamide, sulfonamide, alkylsulfonamide, arylsulfonamide, formyl, alkylacyl, arylacyl, carboxy and its alkyl and aryl esters and amides; or R6 and R7 together are alkylene or heteroalkylene and, with the carbons to which they are attached, are a cycloalkyl, aryl or heterocycle ring, and R8 is hydrogen.

3. The compound of claim 2 wherein:

(a) R1 is unsubstituted $C_1$–$C_6$ linear, or $C_3$–$C_6$ branched or cyclic, alkanyl; or unsubstituted $C_2$–$C_6$ linear, or $C_3$–$C_6$ branched or cyclic, alkenyl having one double bond;

(b) R2 is selected from the group consisting of hydrogen; unsubstituted $C_1$–$C_6$ linear, or $C_3$–$C_6$ branched or cyclic, alkanyl; and unsubstituted $C_2$–$C_6$ linear, or $C_3$–$C_6$ branched or cyclic, alkenyl having one double bond;

(c) R3, R4 and R5 are each independently selected from the group consisting of hydrogen, halo, $C_1$–$C_4$ alkyl, hydroxy, $C_1$–$C_4$ alkoxy, thio, $C_1$–$C_4$ alkylthio, $C_1$–$C_4$ mono- or dialkylamino, $C_1$–$C_4$ alkylacyl;

(d) one of R6 and R7 is bonded at the 8 position, the other at the 9 position, of the fused rings; R6 is selected from the group consisting of alkoxy, alkylthio, monoalkylaminio, dialkylamino, the alkyl portions thereof being saturated and unsubstituted and having from 1 to about 4 carbon atoms; R7 is selected from the group consisting of hydrogen, alkoxy, alkylthio, monoalkylamino, dialkylamino, the alkyl portions thereof being saturated and unsubstituted and having from 1 to about 4 carbon atoms; or the alkyl portions of R6 and R7 are connected forming an alkylene moiety of from 1 to about 4 carbon atoms; R8 is hydrogen;

(e) R9 is selected from the group consisting of hydrogen, halo, $C_1$–$C_4$ alkyl, and phenyl;

(f) R10 and R12, and R11 and R13 if they exist, are each independently hydrogen or $C_1$–$C_4$ alkyl.

4. The compound of claim 3 wherein R2, R10 and R12, and R11 and R13 if they exist, are all hydrogen.

5. The compound of claim 3 wherein R6 and R7 are both $C_1$–$C_4$ alkoxy or $C_1$–$C_4$ alkylthio.

6. The compound of claim 4 wherein R6 and R7 are both $C_1$–$C_4$ alkoxy or $C_1$–$C_4$ alkylthio.

7. The compound of claim 5 wherein R6 and R7 are both methoxy.

8. The compound of claim 6 wherein R6 and R7 are both methoxy.

9. The compound of claim 3 wherein the $C_\alpha$—$N_\beta$ bond is a single bond.

10. The compound of claim 6 wherein the $C_\alpha$—$N_\beta$ bond is a single bond.

11. The compound of claim 8 wherein the $C_\alpha$—$N_\beta$ bond is a single bond.

12. The compound of claim 9 wherein the $C_5$–$C_6$ bond is a single bond.

13. The compound of claim 10 wherein the $C_5$–$C_6$ bond is a single bond.

14. The compound of claim 11 wherein the $C_5$–$C_6$ bond is a single bond.

15. The compound of claim 6 wherein R3, R4 and R5 are selected from the groups consisting of: from one to three of R3, R4 and R5 being independently selected from F, Cl and Br, the other(s) being hydrogen; from one to three of R3, R4 and R5 being independently unsubstituted methyl or unsubstituted methoxy, the other(s) being hydrogen; and one or two of R3, R4 and R5 being independently trifluoromethyl or trifluoromethoxy, the other(s) being hydrogen or fluoro.

16. The compound of claim 14 wherein R3, R4 and R5 are selected from the groups consisting of: from one to three of R3, R4 and R5 being independently selected from F, Cl and Br, the other(s) being hydrogen; from one to three of R3, R4 and R5 being unsubstituted methyl, the other(s) being hydrogen; and one or two of R3, R4 and R5 being trifluorolmethyl, the other(s) being hydrogen.

17. The compound of claim 3 wherein R1 is methyl.

18. The compound of claim 8 wherein R1 is methyl.

19. The compound of claim 13 wherein R1 is methyl.

20. The compound of claim 15 wherein R1 is methyl.

21. A composition comprising:

(a) a safe and effective amount of a compound of any of claims 1, 3, 13 and 20; and (b) a pharmaceutically-acceptable excipient.

22. A method for treating or preventing congestive heart failure or hypotension comprising administering to a human or lower animal in need thereof a safe and effective amount of a compound of any of claims 1, 3, 13 and 20.

23. A method for treating or preventing cardiac arrhythmia or cardiac reperfusion injury comprising administering to a human or lower animal in need thereof a safe and effective amount of a compound of any of claims 1, 3, 13 and 20.

24. A method for treating or preventing a disease or disorder caused by cellular protein transport including, but not limited to, osteoporosis, rheumatoid arthritis, allergic responses, restenosis, vascular tone, cancer, Kaposi's sarcoma, psoriasis, and bacterial infections, comprising administering to a human or lower animal in need thereof a safe and effective amount of a compound of any of claims 1, 3, 13 and 20.

25. A method for treating or preventing nasal congestion or migraine comprising administering to a human or lower animal in need thereof a safe and effective amount of a compound of any of claims 1, 3, 13 and 20.

* * * * *